(12) United States Patent
Altarac

(10) Patent No.: US 9,358,376 B2
(45) Date of Patent: Jun. 7, 2016

(54) MICRONEEDLE ROLLER

(71) Applicant: Ormedix, Inc., Irvine, CA (US)

(72) Inventor: Moti Altarac, Irvine, CA (US)

(73) Assignee: Ormedix, Inc., Irvine, CA (US)

( * ) Notice: Subject to any disclaimer, the term of this patent is extended or adjusted under 35 U.S.C. 154(b) by 0 days.

(21) Appl. No.: 14/577,808

(22) Filed: Dec. 19, 2014

(65) Prior Publication Data

US 2015/0231382 A1    Aug. 20, 2015

Related U.S. Application Data

(60) Provisional application No. 61/918,598, filed on Dec. 19, 2013.

(51) Int. Cl.
*A61B 17/20* (2006.01)
*A61M 37/00* (2006.01)

(52) U.S. Cl.
CPC ... *A61M 37/0015* (2013.01); *A61M 2037/0023* (2013.01); *A61M 2037/0046* (2013.01)

(58) Field of Classification Search
CPC .................. A61M 2037/0023; A61M 37/0015
USPC .................................. 604/47, 46, 173, 21, 22
See application file for complete search history.

(56) References Cited

U.S. PATENT DOCUMENTS

2010/0256594 A1* 10/2010 Kimmell ........... A61M 37/0015
                                                                                 604/506

* cited by examiner

*Primary Examiner* — Phillip Gray
(74) *Attorney, Agent, or Firm* — Rimas T. Lukas

(57) ABSTRACT

A micro-needle roller infusion system for transdermal or intradermal delivery of active agents, skin-care products, and other topical formulations is provided. The infusion system comprises a needle roller assembly with needles enclosed in a housing with a disposable cartridge having the active agent. The device offers the advantages of creating a path for the active agents to reach or be injected into the desired depth for an easier, more effective interaction with the target skin layer. Apart from the approximation of the agent to the target, the device also provides biological benefits of the needling therapy of collagen generation and skin rejuvenation coupled with superior convenience and ease of use.

9 Claims, 10 Drawing Sheets

MICRONEEDLE ROLLER

FIELD OF THE INVENTION

The present invention is directed to a device for the delivery of material or stimulus to targets within a body to produce a desired response, and in particular, to a dermal or transdermal delivery device including a number of projections or microneedles for the penetration or non-penetration of a body surface, delivery of bioactive substances, skin-care products, topical formulations, and other stimuli to living cells and intercellular matrix.

BACKGROUND OF THE INVENTION

Human skin is the largest organ in the body and is made up of multiple layers of ectodermal tissue. Skin regulates temperature and serves as a barrier against foreign agents, toxic substances, microorganisms, pathogens, and injury guarding the underlying muscles, bones, ligaments and internal organs. Human skin varies in thickness from location to location and can be as thin as 0.5 mm on the eyelids and as thick as 4 mm in the soles, palms and scalp. The skin is composed of two primary layers, the epidermis and the dermis. As shown in FIG. 1, the epidermis includes the outermost layers of the skin and forms a protective barrier responsible for keeping water and essential elements in the body and preventing pathogens and foreign substances from entering. The epidermis is subdivided into additional layers that include, beginning with the outermost layer and extending deeper into the skin, the stratum corneum, stratum granulosum, stratum lucidum, stratum spinosum, and stratum basale. The epidermis contains no blood vessels and cells in the deepest layers of the epidermis are nourished by diffusion from blood capillaries extending to the upper layers of the dermis.

The epidermis and the dermis are separated by a thin sheet of fibers called the basement membrane which controls the traffic of cells and molecules between the dermis and the epidermis but also serves, through the binding of a variety of cytokins and growth factors, as a reservoir for their controlled release during physiological remodeling or repair processes. The dermis includes many nerve endings and it also contains the hair follicles, sweat glands, sebaceous glands, lymphatic vessels and blood vessels which provide nourishment and waste removal from its own cells as well as for the epidermis. The top area of the dermis adjacent to the epidermis is called the papillary region and the deeper area is known as the reticular region. The papillary region includes papillae or fingerlike projections that extend toward the epidermis and interdigitates with the epidermis strengthening the connection between the two layers of skin. The reticular region lies deeper and includes collagenous, elastic and reticular fibers that provide strength and elasticity. Also located within the reticular region are the roots of the hair and sweat glands and blood vessels. Beneath the dermis is the subcutaneous fat layer.

Penetration of the outer layers of skin to deliver a pharmaceutical composition is a widely held practice. FIG. 2 illustrates the penetration depths to reach certain layers of the skin. Approximately 0.25 mm penetrates the stratum corneum, approximately 0.5 mm from the outer surface reaches the middle of the epidermis, approximately 1.0 mm to approximately 2.0 mm reaches the basal layer; and approximately 2.5 mm penetrates the top of the dermis layer. In some applications, the bioavailability of an active ingredient may be increased with increased depth of penetration of the microneedles and hence, depth of delivery of the active ingredient.

Typically, injections of pharmaceuticals are achieved by subcutaneous delivery, intramuscular delivery, as well as intravenous delivery. Less invasive procedures have been developed and are also widely utilized. Among these less invasive procedures include topical applications such as patches, which are used to provide slow release of a composition. However, these patch delivery systems rely on formulations that can carry the active ingredients across the skin barrier into the blood stream. Therefore, there is a need for an article of manufacture that can be used to deliver a composition cutaneously or subcutaneously to the skin in a controlled and a convenient way that could be used by professionals or lay users. Specifically, there is also a need for an article that is capable of lancing the surface of skin or is capable of penetrating the surface of skin to a desired depth where a composition can be efficaciously applied.

One solution is the use of microneedles in which each individual microneedle is designed to puncture the skin up to a predetermined distance, which typically is desired to be greater than the nominal thickness of the stratum corneum layer of skin (the very outer layer of the skin out-covering the epidermis). Using such microneedles provides a great benefit in that the barrier properties of the skin are largely overcome. At the same time, the microneedles are relatively painless and bloodless if they are made to not penetrate through the epidermis, which is approximately less than 2.0-2.5 mm beneath the outer surface of the skin.

Microneedles require a direct pushing motion against the skin of sufficient force to penetrate completely through the stratum corneum. Furthermore, when the stratum corneum is penetrated, it is important to efficiently compel a matrix such as a liquid drug or other active ingredient though the relatively tiny openings created by the microneedles as the microneedles are usually quite small in diameter.

In general, microneedle stimulation systems are well known for their use in skin care treatment of various conditions such as wrinkles, acne scarring, stretch marks, skin whitening and facial rejuvenation. In microneedling, a method of piercing holes in the skin and applying drugs or cosmetics to the skin provides a way to rapidly and sufficiently permeate the skin. Another advantage of using microneedles is to injure the skin just enough to begin natural healing processes and stimulate collagen and elastin production, and the like, to heal the skin. In these methods, hundreds to thousands of tiny holes or microconduits are created in the skin with the microneedling device without damaging the deeper layers of the skin. This injury to the skin begins a natural healing process that leads to the release of natural stimulants and growth factors which stimulates the formation of new natural collagen and elastin in the papillary dermis to produce new, healthy skin tissue. Also, new capillaries are formed. This neovascularisation and neocollagenesis associated with the wound healing process leads to the formation of younger looking skin, reduction of skin pathologies and improvement of scars. Generally called percutaneous collagen induction therapy, microneedling has also been used in the treatment of photo ageing. Furthermore, medical substances may be applied to the site where the holes are created and the substances are supposed to permeate into the skin through the tiny holes. Microneedling is generally applied to the face, neck, scalp, and just about anywhere on the body where a particular condition warrants without removing or permanently damaging the skin. Microneedling is simple and safe. A predetermined number of needles are inserted into the skin to the desired depth. As a reaction to the minor injury, the skin tissue begins a natural wound-healing cascade. This natural process forms new healthy dermal tissue that helps smooth scars, remove wrinkles and improve pigmentation, and yields a younger, healthier and a cleaner-looking skin.

There is a need for an improved microneedling system. The present invention provides an improved microneedle roller system for mechanically perforating the outer skin layer in the presence of one or more active agents in a controlled environment that allows for approximation and absorption of the active compounds in a stable delivery environment. It is an object of the present invention to provide an improved microneedle mechanical delivery system that can provide a greater efficiency of flow from the device for one or more types of compounds topically and/or through the stratum corneum, and to the have the delivery system penetrate and stimulate the outer skin layers by a rolling motion across the skin at the same time.

SUMMARY OF THE INVENTION

The microneedle roller system of the present invention provides improved delivery of one or more active agents to the skin of a subject. The microneedle roller system generally comprises a housing having one or more cavities, wherein each cavity is adapted to receive one or more containers, reservoirs, cartridges and/or one or more active agents contained in the cavity or in the containers, reservoirs or cartridges that may be removable, interchangeable or replaceable. The housing encloses a skin penetrating device that is in fluid connection with the cavity in the housing. The skin penetrating device comprises a microneedle roller comprising one or more microneedles attached to and supported by a roller surface wherein movement of the roller over the skin of the subject causes a rotation of the roller and brings the microneedles into contact with the skin of the subject through an opening in the assembly resulting in penetration of the skin and the transdermal or dermal delivery of the active agent, the skin care product, the topical formulation, stimulation or combinations thereof present on or provided by the roller. The active agent comprises a formulation selected from the group including but not limited to a solution, a suspension, an emulsion, a lotion, a hydrgel, a semi-solid formulation, a cream and an emollient. In another aspect the active agent comprises a therapeutic or a prophylactic drug, wherein the drug is selected from the group including but not limited to of analgesic agent, an anti-inflammatory agent, an anti-allergic agent, a steroid, a local anesthetic, a muscle relaxant, a neurotoxin, an anti-itch agent, an anti-bacterial agent, an anti-fungal agent, vaccines, hormones, systemic drugs, dermatological active agents, herbal products, homeopathic preparations and combinations and modifications thereof. The device offers the advantages of creating a path for the active agents to reach or be injected into the desired depth for an easier, more effective interaction with the target skin layer. Apart from the approximation of the agent to the target, the device provides the well-known biological benefits of the needling therapy of collagen generation and skin rejuvenation coupled with superior convenience and ease of use.

DETAILED DESCRIPTION OF THE INVENTION

Turning to FIGS. 3-17, there is shown a microneedle roller device 20 according to the present invention. The microneedle roller 20 includes a handle 22 connected to a housing 24 at the distal end. The housing 24 may be permanently affixed to the handle 22 or may be configured to be removed and interchanged with another housing 24 such as a larger housing having a larger or longer roller or to replace a used housing with a new housing after use or with a housing having a roller with different needle lengths. The housing 24 may be connected via a spring or ball joint to allow the housing 24 to move easily up and down or right or left to adjust to the surface contours of the body in order to create a smooth movement over different anatomical areas.

Figure 1:
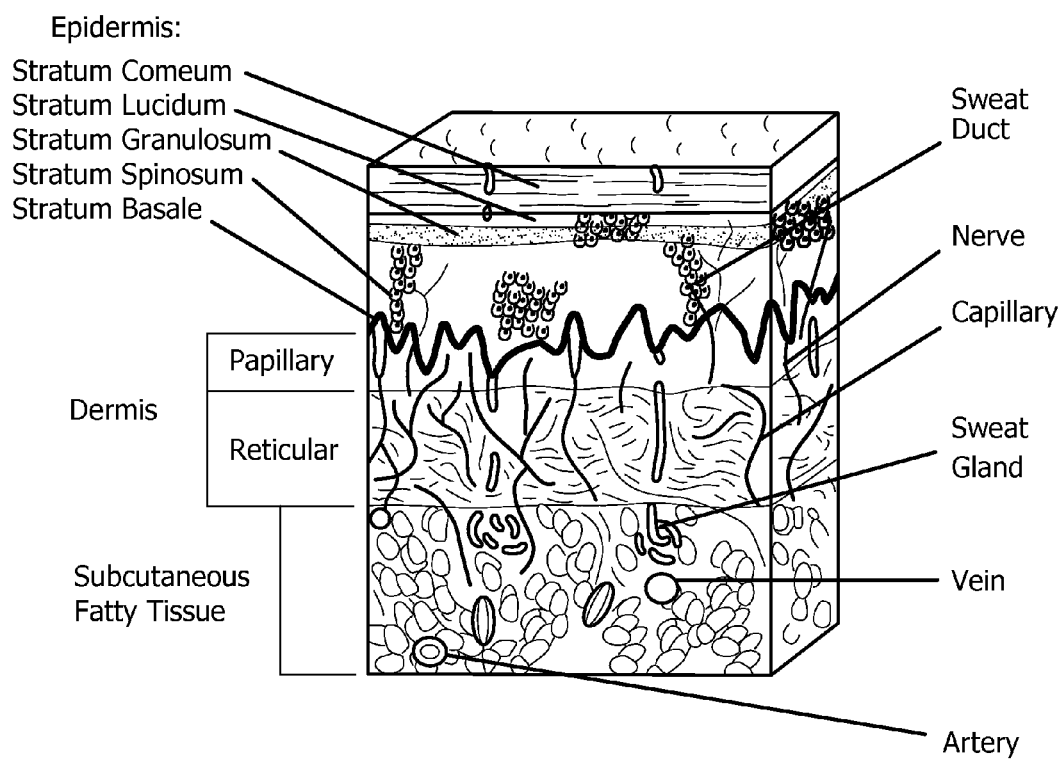
FIG. 1 is a top perspective view of various layers of human skin.
Figure 2:
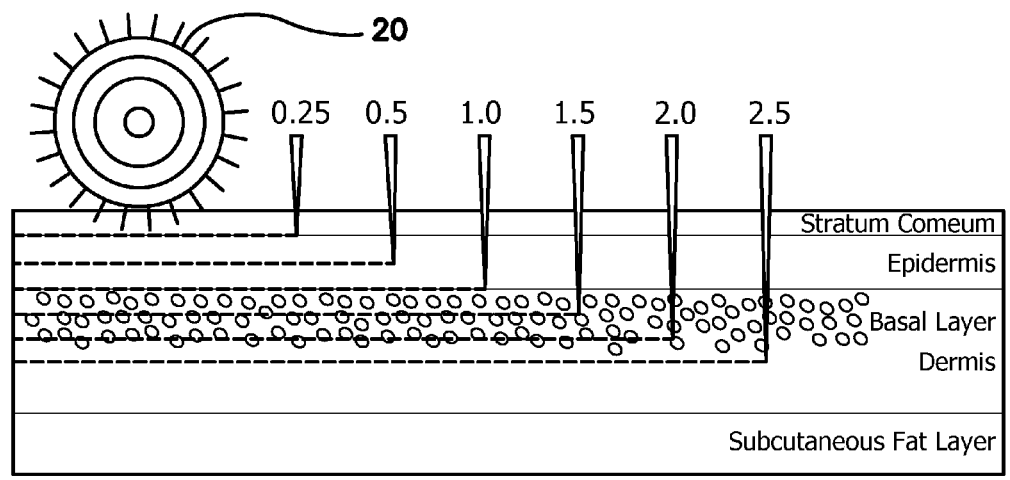
FIG. 2 is a schematic of a side view of a microneedle roller and various layers of skin and their depths from the surface.
Figure 18:
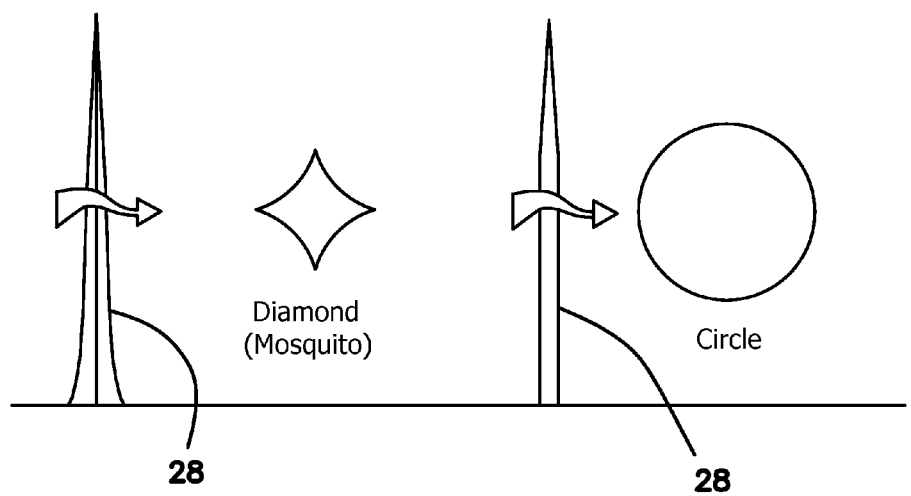
FIG. 18 is a schematic of a microneedle and its cross-section according to the present invention.
Figure 3:
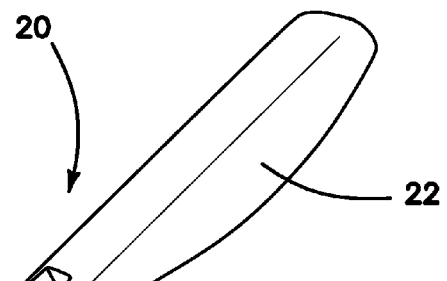
FIG. 3 is a top perspective view of a microneedle device according to the present invention.
Figure 4:
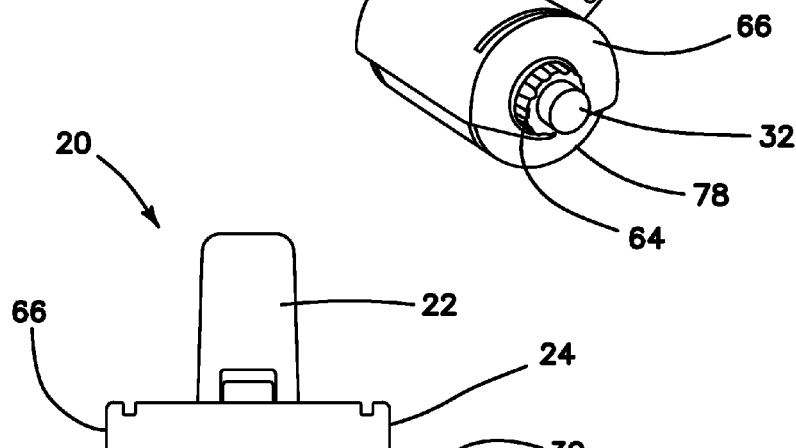
FIG. 4 is a front view of a microneedle device according to the present invention.
Figure 5:
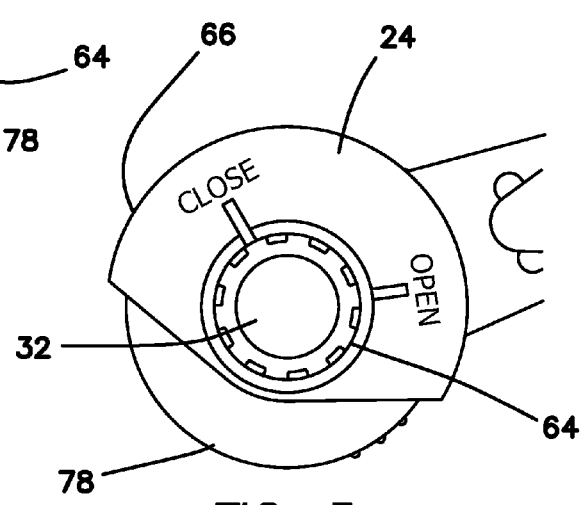
FIG. 5 is a side, partial view of a microneedle device according to the present invention.
Figure 6:
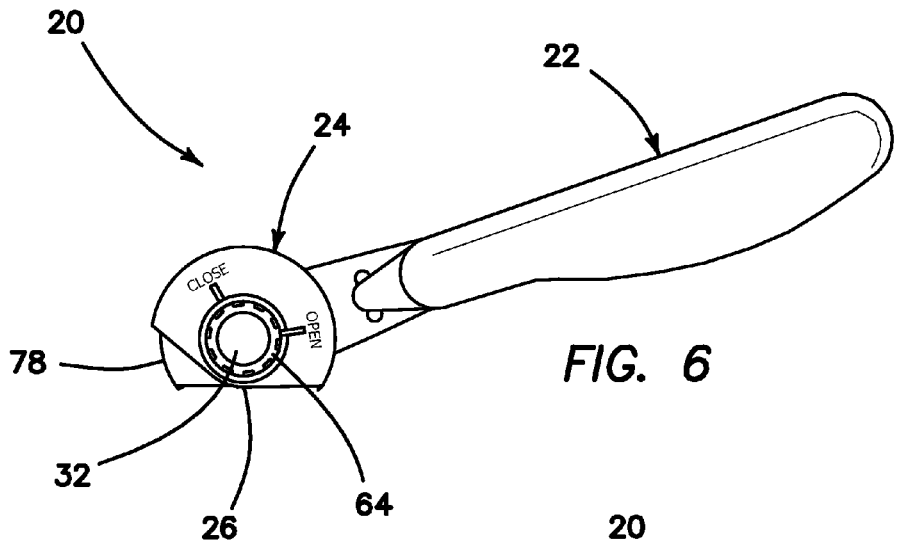
FIG. 6 is a side, partial view of a microneedle device with a sliding door in an open position exposing the skin penetrating device according to the present invention.
Figure 7:
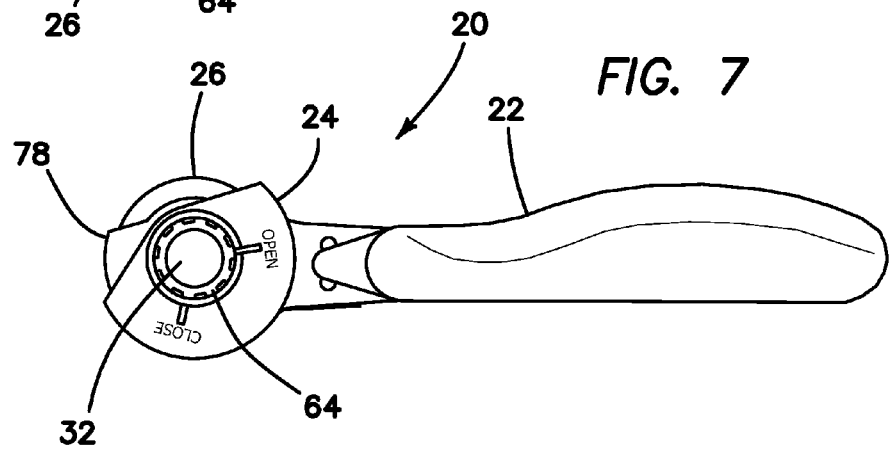
FIG. 7 is a side, partial view of a microneedle device with a sliding door in an open position exposing the skin penetrating device according to the present invention.
Figure 9:
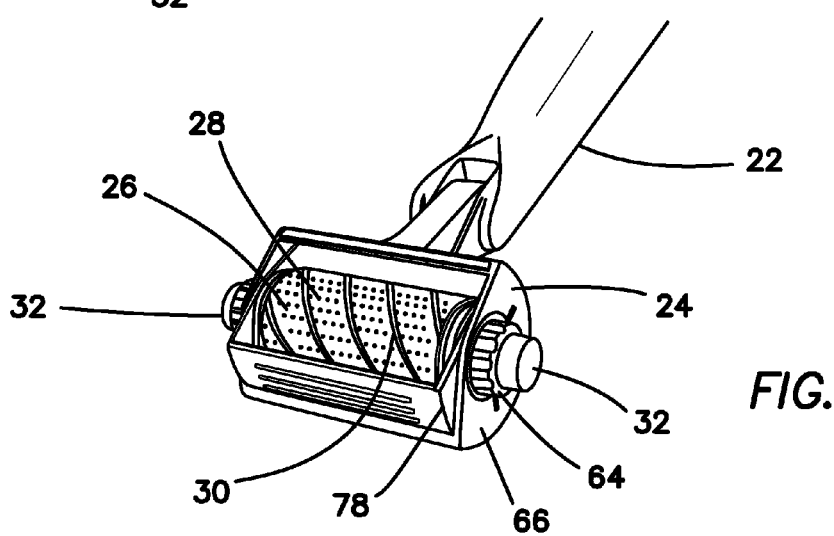
FIG. 9 is a bottom, partial perspective view of a microneedle device with a door open showing the skin penetrating device according to the present invention.

The housing 24 includes a skin-penetrating device 26 that is in fluid communication with at least one cavity in the housing 24. The skin-penetrating device 26 is a microneedle roller. The microneedle roller 26 is a cylinder having an outer surface provided with a plurality of very small needles or microneedles 28 extending outwardly from the outer surface. The microneedles 28 have a sharp distal end configured for mechanically perforating the outer skin layer. The proximal end of a microneedle 28 is embedded in the microneedle roller 26. The length of the microneedle 28 that extends beyond the outer surface may be preselected or predetermined for the particular application for which the device is suited and designed for such as a roller having longer needles for penetrating deeper into the skin layers relative to a roller having shorter needles. The proximal end of a microneedle 28 may taper toward the distal end to create a sharp point or tip near the distal end. The microneedles 28 are made by reactive ion etching techniques of stainless, surgical steel or titanium metal or other alloy or plastic or appropriate material and do not necessarily be configured to penetrate the skin. The microneedles 28 are embedded into the outer surface of the cylindrical roller 26 which may be made of a resin, soft plastic, silicone or other polymer layer which may be molded over the needles 28. A plurality of microneedles 28 are arranged in an array around the cylindrical outer surface of the roller 26 at a density of approximately 1-250 microneedles per square centimeter. When the roller 26 is rolled across the skin surface, they are configured to pierce the skin and penetrate the stratum corneum and create microconduits for fluidic transport into and/or across the stratum corneum. The microneedles 28 may be small enough to provide adequate stimulation of skin layers or large enough to create micrometer scale pathways across the skin for drug delivery of even the largest macromolecules. In another variation, the microneedles 28 are cannulated to provide a fluidic pathway through the needle 28 to an exit aperture at the tip of the needle 28. In another variation, the cross-section of a needle taken perpendicular to the longitudinal axis of the needle may not only be circular but also diamond-shaped including a diamond shape having curved sides as shown in FIG. 18. In another variation, the needle 28 includes plastic mushroom heads to apply blunt pressure on the skin to create a micro-massaging effect and in another version non-penetrating, blunt-tipped, or mushroom-capped needles made of plastic or resin, for example, can provide local needling stimulation of the skin without penetrating it while applying topically the desired agents. The non-penetrating needles can be used for reflexology or massage. The outer surface of the cylinder 26 includes a spiral channel 30 for evenly distributing material across the outer surface of the roller 26 and onto the skin from the at least one cavity of the housing. The skin penetrating roller 26 includes an inner lumen for connection with at least one pin 32 inserted into the lumen. FIGS. 3-17 show two pins 32 inserted into either end of the lumen and configured for the rotation of the roller 26 relative to the housing 24. In one variation, a spring 34 is used to bias at least one of the pins 32 so that compression of the pins 32 inwardly will release the roller 26 from the housing for replacement or interchangeability with another roller 26. The housing 24 further includes a first gear 36 connected to one of the pins 32 such that rotation of the roller 26 rotates the pin 32 which in turn rotates the first gear 36.

Figure 10:
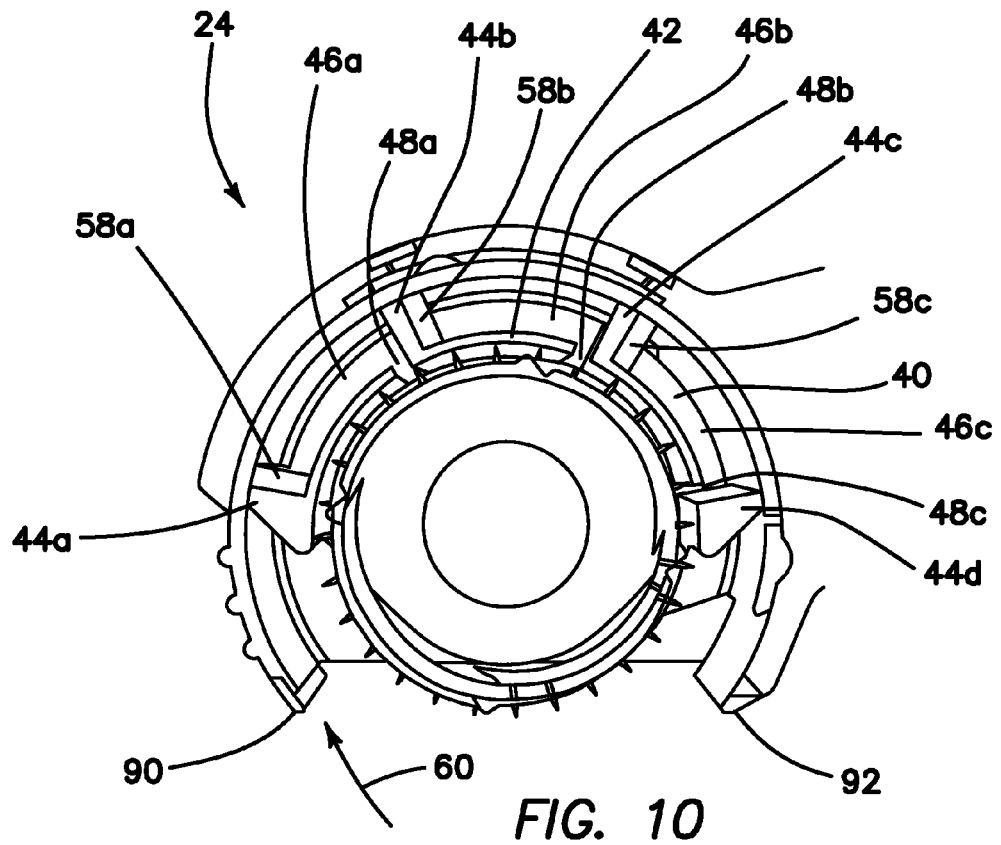
FIG. 10 is a partial, side cross-sectional view of a according to the present invention.
Figure 12:
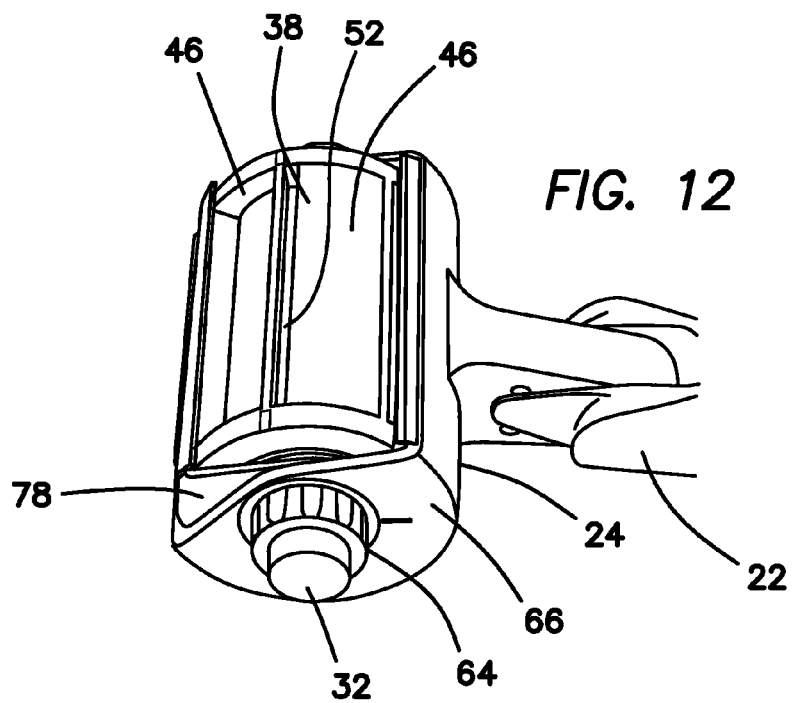
FIG. 12 is a partial bottom perspective view of a microneedle device in a load position according to the present invention.
Figure 11A:
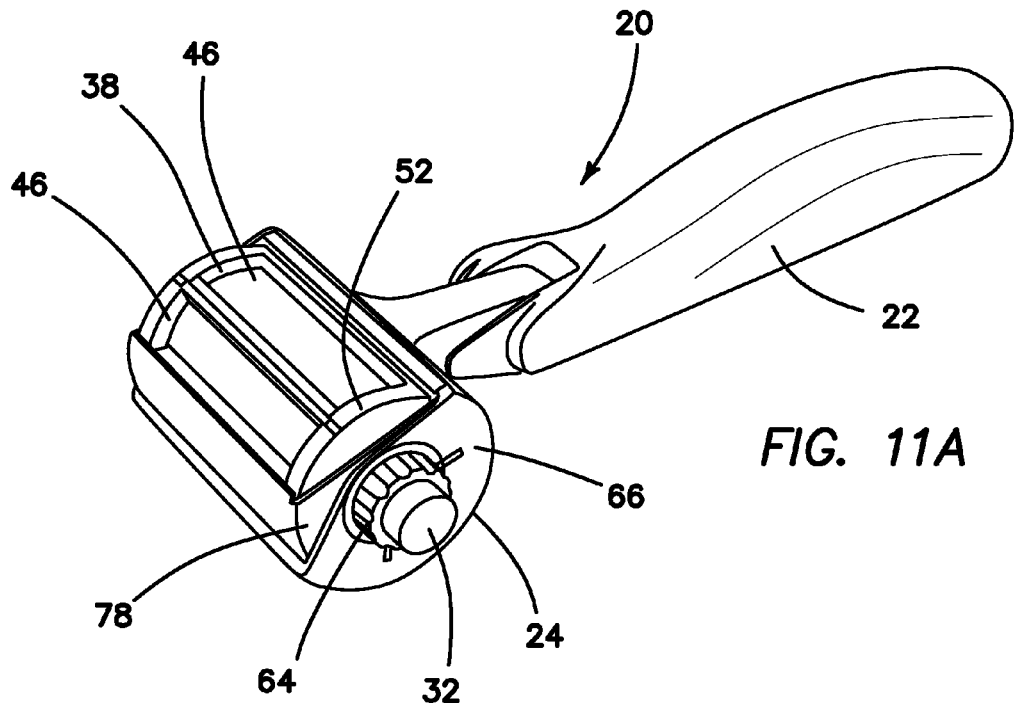
FIG. 11 is a bottom perspective view of a microneedle device according to the present invention.
Figure 11B:
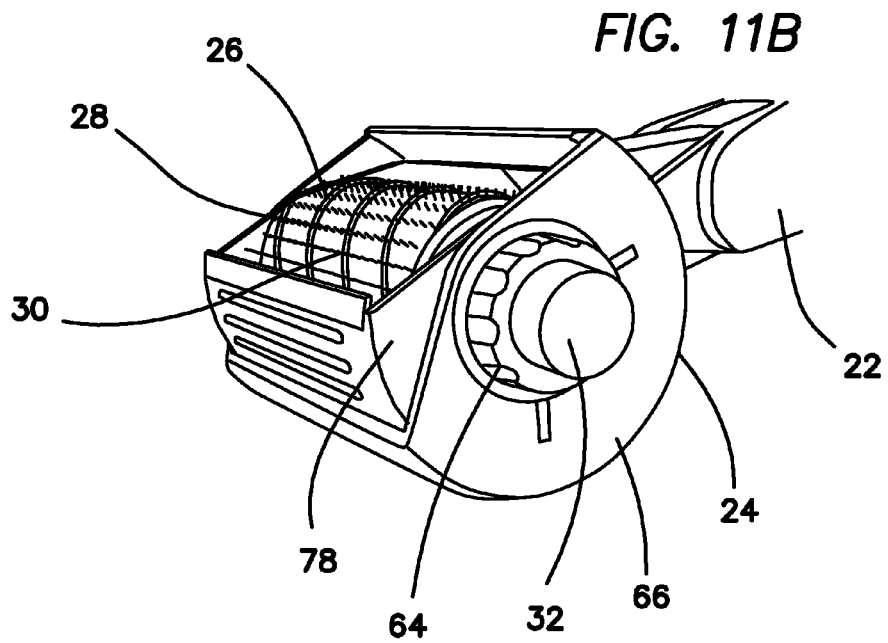
Figure 13:
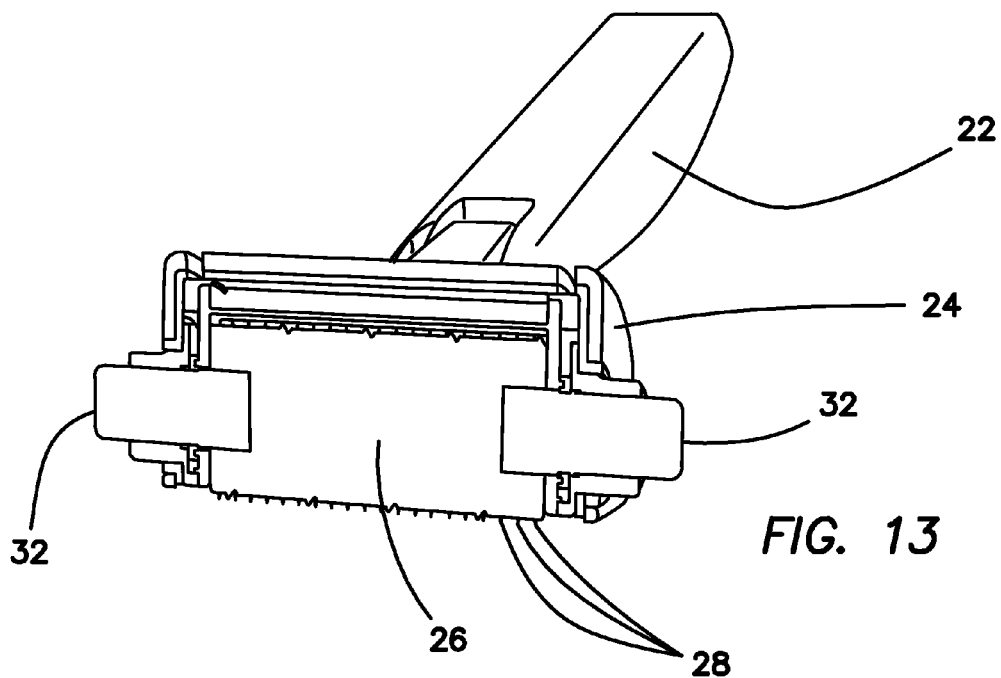
FIG. 13 is a top perspective, cross-sectional view of a microneedle device according to the present invention.
Figure 14:
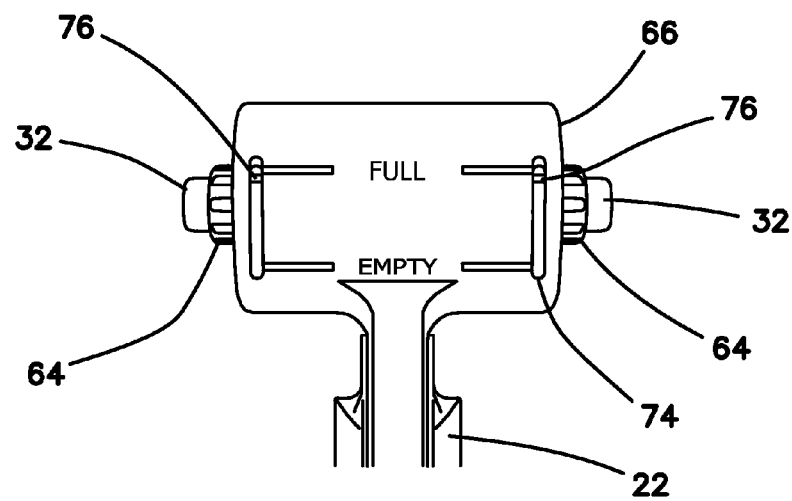
FIG. 14 is a top partial view of a microneedle device according to the present invention.
Figure 15:
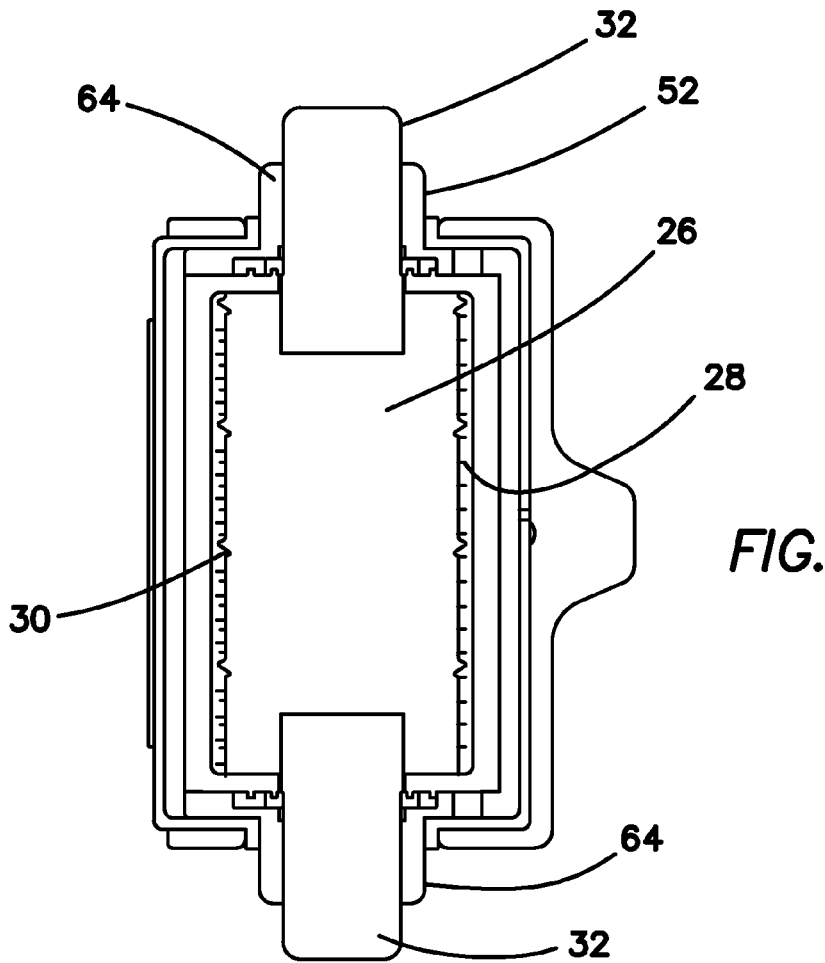
FIG. 15 a partial cross-sectional view of a microneedle device according to the present invention.

The housing 24 of the device 20 further includes a chamber element 38. The chamber element 38 includes two oppositely disposed end caps 40 that are spanned by a bottom wall 42 at least two side walls 44. The end caps 40 serve as end walls which together with the bottom wall 42 and the two side walls 44 define a cavity 46. In one variation that is shown in FIG. 10, three cavities 46a, 46b, 46c are defined by the two end caps 40, bottom wall 42 and four side walls 44a, 44b, 44c, 44d. The sidewalls 44 extend radially upwardly from the bottom wall 42 to define the height of the cavity 46. The distance between the side walls 44 define the width of the cavity 46 and the distance between the end caps 40 define the depth of the cavity 46. The cavity space may be varied. Each cavity 46 includes a slot 48 that is formed in the bottom wall 42. In one variation, the slot 48 extends from end cap to end cap 40 along the entire depth of the cavity 46. The slot 48 serves as an exit portal for material exiting the cavity 46. FIG. 10 shows three cavities 46a, 46b, 46c with each cavity having its own slot 48a, 48b, 48c, respectively. The chamber element 38 includes two circular apertures 51 formed in the end caps 40. The pins 32 extend through these apertures 51 to connect the roller 26 to the chamber element 38 such that the roller 26 can rotate relative to the chamber element 38. A second gear 50 is connected to the outer surface of one end cap 40 on the same side of the chamber element 38 as the first gear 36. This second gear 50 is configured to connect with the first gear 36 such that rotation of the first gear 36 moves the second gear 50 along a rack 54 of a pusher element 52 of the housing 24.

Figure 8:
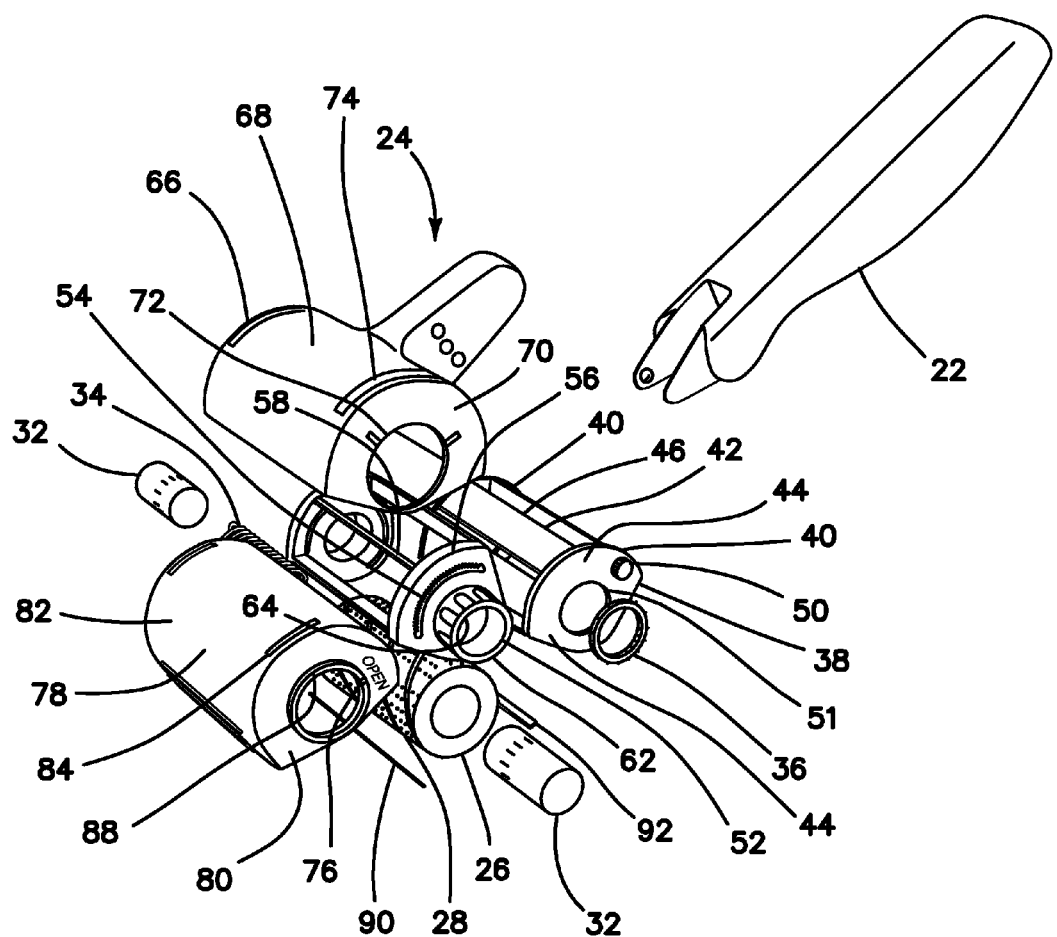
FIG. 8 is an exploded perspective view of a microneedle device according to the present invention.

The pusher element 52 includes a rack 54 having teeth for engaging with the second gear 50. As the roller 26 rolls across the surface of the skin, it rotates the first gear 36 which in turn moves the second gear 50 along the rack 54 moving the pusher element 52 relative to the chamber element 38. As shown in FIG. 8, the pusher element 52 includes two pusher end caps 56. At least one of the end caps 56 includes a rack 54 comprising an open slot with teeth configured for engagement with the second gear 50. At least one pusher 58 spans the two pusher end caps 56. The pushers 58 are side walls that extend radially relative to the pusher end caps 56. FIG. 10 illustrates a pusher element 52 having three pushers 58a, 58b, 58c spanning the pusher end caps 56. The three pushers 58a, 58b, 58c are spaced apart from each other such that when the chamber element 38 is disposed inside the pusher element 52, the pushers 58a, 58b, 58c extend into each cavities 46a, 46b, 46c, respectively. When the roller 26 rotates, the pushers 58 will move in the direction of the arrow 60 across the length of the cavity 46. The pushers 58 are configured to squeeze or push material along the length of the cavity 46 and out of the cavity 46 through slots 48. The pusher end caps 58 include apertures 62 configured for the passage of pins 32. Knobs 64 that extend outwardly from the pusher end caps 56 are formed in the location encompassing the pusher apertures 62. The knobs 64 permit rotation of the pusher element 52 into position to load and unload the cavities 46.

The housing 24 further includes a housing cover 66. The housing cover 66 has a proximal end with means for attachment to the handle 22. The housing cover 66 is partially cylindrical in shape having an outer wall 68 interconnected with opposite end walls 70. Each end wall 70 includes an aperture 72 for passing of pusher knobs 64 and pins 32. The outer wall 68 includes at least one window 74 through which a marker 76 on the pusher element 52 is visible. Visibility of the marker 76 provides visual indication of how far along the length of the cavity 46 a pusher 58 has travelled, thereby, indicating to the user whether the cavity 46 is full or empty. The outer surface of the outer wall 68 also is provided with markings such as "FULL" and "EMPTY". The housing cover 66 is partially cylindrical to provide an opening through which the needle roller 26 may extend. The opening is closed with a sliding door 78.

The housing 24 further includes a sliding door 78. The sliding door 78 is configured to connect with the housing cover 22 and to slide between an open position uncovering and exposing the needles 28 and a closed position covering the needles 28. The sliding door 78 is also partially cylindrical in shape having partially circular end walls 80 interconnected by a partially cylindrical outer wall 82. The outer wall 82 includes windows 84 that are aligned with the at least one window 74 in the housing cover 66 to permit visibility of the marker 76 on the pusher element 52. The end walls 80 also include circular apertures 86 for the passage of pins 32 and knobs 64. The perimeter of the apertures 86 are provided with markers 88 that provide indication to the user whether the door 78 is open or closed. Markings such as "OPEN" and "CLOSED" are provided on the end walls 70 of the housing cover 66. The housing 24 or skin penetrating cylinder 26 may be varied with narrower width housings 24 or cylinders 26 used for smaller application areas in order to cover areas that are harder to cover with a wider housing 24 or cylinder 26. The housings 24 may be removable and interchangeable with the handle 22 according to the intended use. Also the density of the microneedles 28 may vary from one skin penetrating cylinder 26/housing 24 to another with the size of the skin penetrating cylinder 26 remaining constant or varying in size. The cylinder 26 or housing 24 may be interchanged with another cylinder 26 or housing 24 having a different microneedle density that is more suitable for the intended purpose or the severity of the treated skin condition.

The housing 24 is assembled by passing pins 32 into the lumen of the cylindrical roller 26, one or more of which may be spring biased such that the pins 32 may be depressed relative to the roller 26 so that the roller may be released from the housing 24. The roller 26 and pins 32 are disposed through the apertures 51 in the chamber element 38 and through the apertures 62 in the pusher element 52 and through the apertures 86 of the door 78 and through the apertures 72 of the cover 66. The chamber element 38 is disposed within the pusher element 52 such that the first gear 36 contacts the second gear 50 which is connected to the rack 54 of the pusher element 52. The door 78 is snapped into the housing cover 66 such that the door is movable between an open position and a closed position. The knobs 64 of the pusher element 52 can be turned between a first open position for loading the cavities 46 with material for dispensing and a second closed position indicating a loaded position.

In operation, the microneedle roller device 20 is turned over and the sliding door 78 of the housing 24 is opened to expose the skin penetrating device or roller 26. The sliding door 78 protects the user from inadvertent puncturing with the microneedles 28 and prevents drying out of the material. The knobs 64 are turned to expose the cavity 46 through the opening in the housing cover 66. The at least one cavity 46 is loaded with material. The material may be directly loaded into the cavity 46 or provided in cartridges or pouches or other container such as a capsule in which case the container is placed into each cavity 46. The knobs 64 are turned to rotate the cavities 46 into the loaded position and expose the microneedles 28. The exposed microneedles 28 are contacted with the skin and the roller 20 is rolled across the skin such that the microneedles 28 penetrate the skin. As the roller 26 rotates, the first gear 36 moves the second gear 50 relative to the rack 54 of the pusher element 52. This action moves the pushers 58 along the length of the cavity 46, thereby, pushing material or squeezing the cartridge or pouch so as to dispense material out of the cartridge or pouch and out of the cavity 46 through the slot 48 and onto the microneedles 28 and roller 26. The first and second gears are metered to dispense the appropriate and desired amount of material onto the roller 26 and the spiral channels 30 in the roller 26 help to even out the material across the roller surface so that material is evenly applied onto the skin. With continues usage, the pushers 58 will move across the length of the cavity 46 until the cavity sidewall 44 is contacted at which point the marker 76 on the pusher element 52 will indicate through the windows 74, 84 that the cavity 46 is empty at which point the user can turn the knob 64 to expose the cavity 46 for reloading. After use, the sliding door 78 of the housing is closed to prevent material from drying out and to protect the user from inadvertent puncturing with the microneedles. In one variation, the roller 26 is configured such that moving the roller 26 in the opposite or backward direction relative to the skin instead of a forward movement will still move the pusher 58 to dispense material. In another variation, backward motion of the roller 26 results in the pusher 58 not moving and no new material being dispensed or pushed out of the cavity 46. Hence, the device 20 can either dispense material only on forward movement or may be configured to dispense material during movement in both the forward and backward directions.

The microneedle roller device 20 may be further provided with a strip 90 located at the front of the device 20 and connected to the housing 24 such that the strip 90 makes contact with the skin prior to the skin coming into contact with the needles 28 of the roller 26 thereby prepping the skin with material. An additional strip 90 may also be placed at the back of the roller 20 after the needles contact the skin. The strip 90 may be provided with material that is an anesthetic to sooth or numb the pain that may be felt from the needles 28 puncturing the skin. Also, the strip 90 may be provided with the same material that is provided in the cavities 46 for extra absorption or any other material in wet or dry form, which may be released upon wetting and/or contact with the surface. The strip 90 may be sponge-like to retain material yet dispense an appropriate amount when in contact with the skin. Also, the strip 90 may be interchangeable and replaced when used. A rubber metering bumper may also be provided at the front of the device to help evenly distribute or smooth the material. To enhance the well-established advantages of microneedling, different active agents can be applied onto the skin prior or after the needling procedure. Such agents include but are not limited to vitamins, minerals, natural plant extracts, hyaluronic acid (HA), cosmetics, pharmaceuticals, moisturizers, homeopathic agents and the like. The material provided via the strips 90 may be the same or different from the material provided via the cavities 46.

The microneedle roller device 20 may be further provided with a collection bar 92 located at the back of the device 20 and connected to the housing 24 such that the collection bar 92 makes contact with the skin after the skin comes into contact with the needles 28. The collection bar 92 serves to collect excess material that may remain on the skin and to cycle the material back onto the roller 26 for re-application onto the skin.

The microneedling roller device 20 of the present invention offers the advantages of the needling therapy and at the same time ensures accurate, standardized and convenient means of delivering the chosen agent into the desired skin layer with the appropriate length needles. The use of the device 20 will provide collagen generation, skin rejuvenation and wound healing effect associated with the needling as well as the additional contribution provided by the adjuvant pharmaceutical/cosmetic agent or agents delivered by the device into the desired skin layer.

The housing 24 of the present device or alternatively the roller 26 may be replaced or sterilized and can carry one or more refillable cavities 26 or no refillable cavities that contain the active agent to be released upon contact with the skin so that the entire housing would have to be replaced with a new sterile housing. Alternatively, the roller 26 and housing 24 may be sterilized by the user employing a sterilizing agent in the form of a dissolvable tablet or liquid into which the housing is immersed.

While the microneedle roller device 20 is rolled over the device, the spring loaded handle 22 allows the housing 24 to adapt to the varying contours of the body. The needles 28 penetrate the skin to the desired layer creating microscopic conduits. The length of the needles determines the skin layer to be affected and the roller with the appropriate needle length is selected by the user accordingly. The dispensing cavities 46 and/or strips 90 release the active agent to the surface of the skin. The agent released by the front strip 90 will be pushed into the micro-openings in the skin created by the needles 28 that touch the skin immediately after. Any agent released by the back strip 90 will passively infiltrate the skin puncture holes. The device 20 may be used without any material to just stimulate the skin into natural collagen production, healing and rejuvenation. The device 20 provides an improvement in the accuracy in terms of the amount of material applied, providing more standardized homogenous application and a more convenient and less messy user experience. Furthermore, two or more active agents may be applied at the same time either by filing the different cavities 46 with different agents or providing the front strip or rear strip with an agent that is different from the agent provided in the cavities 46. This application method will allow for a more efficient use of the active agents together with a better control of the amounts delivered.

Figure 19:
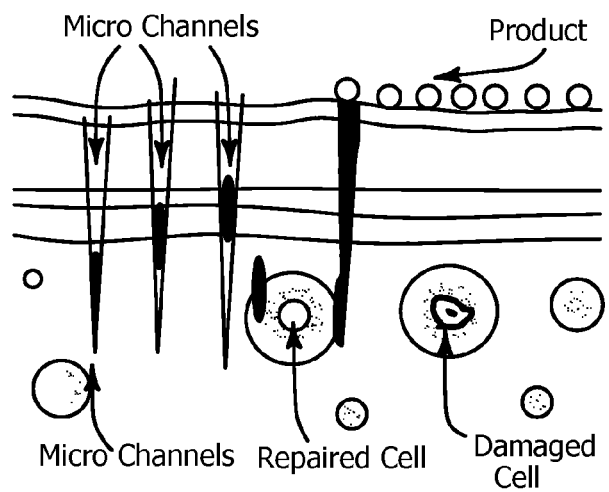
FIG. 19 is a schematic showing micro-channels formed by the microneedles into the skin and product on the surface of the skin entering the micro-channels according to the present invention.
Figure 16:
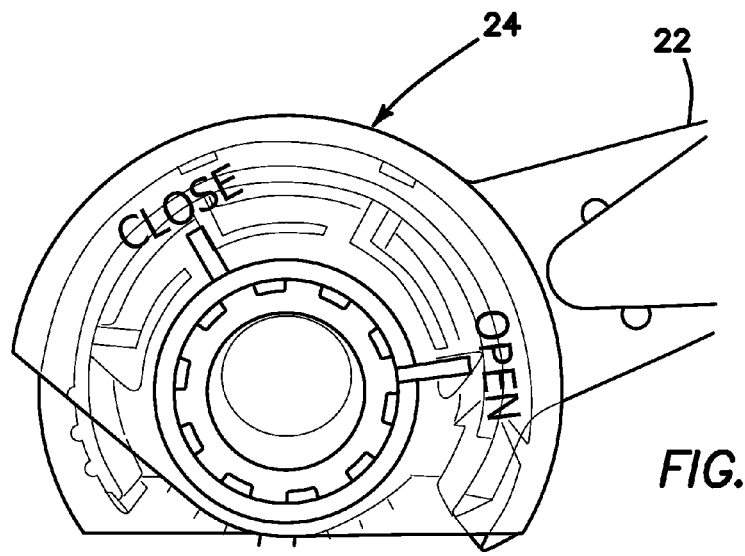
FIG. 16 is a partial, semi-transparent view of a microneedle device according to the present invention.
Figure 17:
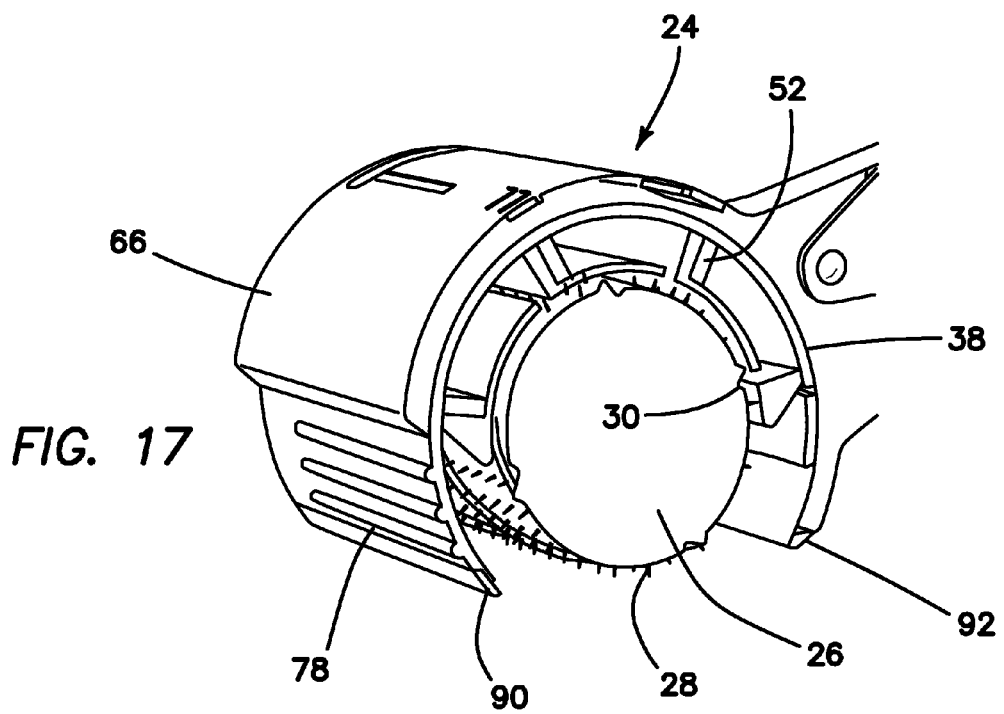
FIG. 17 is a partial, cross-sectional view of a microneedle device according to the present invention.

As described above, the microneedles 28 may be cannulated or hollow so that material may be moved through the needle 28 and out through the tip of the needle. The material delivered to the tip of the needles will be directly injected into the skin layer into which the needles penetrate. The device may include external refillable dispensing chambers that contain an additional agent that would be dispensed onto the surface of the skin upon contact and will provide an additional means for a topical application. The device provides the ability to deliver one agent into the skin via the chambers, the front or back strips. Other features such as vibration of the housing and roller, ion release, heat emission, cooling features, sound (or ultrasound) emission, light (of different wave lengths) emission and electromagnetic discharge may be combined with the device 20. FIG. 19 illustrates micro-channels formed in the skin with product deployed on the surface of the skin migrating through the micro-channels formed by the microneedles 28 and reaching repaired and damaged cells.

The microneedle roller device 20 of the present invention may further include a display configured to present the user with specific information pertaining to the roller such as the distance the device has traveled on the skin, a calculation of the number of needling punctures delivered to the skin, and the amount of substance or dosage injected to the skin that is based on the concentration and the area treated. Sensor and a microprocessor may be included and configured to display the information on a small LCD screen located on the roller. Other information such as time for replacement, sterilization or replacement of medicament cartridge may also be calculated and indicated on the display screen. For example, rolling a particular device 20 for a distance of six inches will deliver a pre-calculated dose to the surface of the skin. The microprocessor can be programmed by the user or physician such that the indicator provides an information to the user that the pre-calculated dose has been delivered and that rolling may cease. Also, the device 20 itself may stop delivery of material from the reservoir chamber by closing off the chamber from dispensing material onto the cylinder. In one variation, the device 20 is configured to vibrate to further assist in projecting the needles into the skin or provide a massaging-effect. Also, vibration of the skin surface helps the material overcome static friction and penetrate or travel a longer, deeper distance into the skin. In such a variation, the vibrating motor may be provided inside the handle 22 or housing 24 or configured such that housing 24 vibrates relative to the handle 22 or such that the surface of the skin is vibrated. The device 20 according to the present invention may include a microprocessor and a transmitter such as a radio frequency or Bluetooth device to transmit information and/or provide control of the device 20 from an external location such as a computer, Internet connection, smart phone or other mobile computing device or tablet. The external device may be provided with a software application that monitors progress, including the storage of before/after photographs, progress notes, providing reminders, dosage changes and recommendations to and from a physician or user community. In another variation, the device 20 may further includes an infra-red light source or heating device located on the device and directed toward the surface of the skin in order to provide an adjuvant treatment modality.

The microneedle roller device 20 of the present invention can be used for cosmetic applications such as skin whitening, dark spots, cellulitis, wrinkle removal, pigmentation removal, melasma, stretch mark removal (apothederm), sun damage skin marks, acne treatment, post acne marks, hair removal agents, uneven skin tone, tattooing, tattoo removal, dry skin, skin hydration, skin tightening, general moisturizing, hand rejuvenation, loose skin, double chin, vitamin delivery, alopecia, hair loss and tanning. For scalp treatment purposes such as the treatment of migraines and hair growth, the microneedles may be longer, bigger and canulated in order to penetrate the thicker skin and to penetrate it more deeply. The microneedle roller device 20 according to the present invention may be configured with specialized needles such as longer or thicker needles for creating micro-channels in the scalp to facilitate the insertion of hair plugs into the scalp in a faster, more-even manner. It may also be used for dermatological conditions such as but not limited to acne, psoriasis, scars, keloids, burns, contractures, alopecia, scales, fungal infections and itching to apply agents like botox, restaline, collagen, steroids, regain, anti-scarring products, lattice and different local antimicrobial anti-fungal and other biologically active agents. Also, the device 20 may be used for medical applications such as immunizations, vaccinations, injections of hormones like insulin, growth factors, fertility supportive hormones, testosterone, local anesthetics, skin cancer, treatment for hemangiomas and varicose veins, colloidal silver, stem cell delivery and any other medical condition requiring controlled delivery of active agents to be used by medical professionals, by patients or by lay people. The needling effects of the device coupled with appropriate agents could be also used for soft tissue augmentation or phallic augmentation.

The device represents advantageous means of delivery of bio-active materials combined with higher convenience and ease of use. The device will also improve the efficacy of the delivered active agents as it creates micro-channels in the skin bringing the agents closer to their targets in the different layers of the skin.

An example for a cosmetic use in which the device may be used is skin-whitening procedures. Most skin-lightening treatments can reduce or block some amount of melanin production and are aimed at inhibiting tyrosinase. Many treatments use a combination of topical lotions or gels containing melanin-inhibiting ingredients along with a sunscreen and a prescription retinoid. Depending on how the skin responds to these treatments, exfoliants, either in the form of topical cosmetic or chemical peels and lasers may be used. For skin whitening, material that may be used with the device include hydroquinone which is the primary topical ingredient for inhibiting melanin production. Its components have potent antioxidant abilities. Topical hydroquinone comes in 2% solution typically available in cosmetics or higher concentrations that would require a prescription, alone or in combination with tretinoin 0.05% to 0.1%. Hydroquinone is a strong inhibitor of melanin production and its effect is on melanin hyper pigmentation. Another material that may be used with this device for skin whitening is azelaic acid which is a component of grains, such as wheat, rye, and barley. It is applied topically in a cream formulation at a 10-20% concentration. It is used to treat acne, but is also effective for skin discolorations by inhibiting the melanin production. Another material is Vitamin C which is considered to be an effective antioxidant for the skin and helps to lighten the skin by elevating glutathione levels in the body. Arbutin, which is found in pears and berries (bearberry, mulberry, white mulberry and paper mulberry), inhibits melanin production and may also be used with this device. Kojic acid is a by-product of rice in the fermentation process of sake. Research shows kojic acid is effective in inhibiting melanin production and as an antioxidant and can be used with the device 20. Kojic acid is unstable in cosmetic formulations as it turns brown and lose its efficacy upon exposure to air or light. Many cosmetic companies use kojic dipalmitate as an alternative because it is more stable in formulations. Since the chambers of the device can host active materials in sealed cartridges, the unstable product can be stored in a vacuum packed cartridge that will maintain its stability until the time of use. Upon application with the device, the cartridge will be initiated (punctured) and the product will be immediately used. The device allows the use of individual single-use cartridges such as at each treatment session the consumer uses only the amount needed while the rest of the material (in other cartridges) does not sustain long term exposure to air or light and by that way the device allows for the use of unstable materials without the waste of unused materials. *Cinnamomum subavenium*, a Chinese herb, is used as a skin whitening agent and may also be used in the present invention. The plant contains substances which inhibit production of tyrosinase an enzyme which catalyzes the production of melanin. Other commercially available skin whitening products such as Aveeno Positively Radiant Daily Moisturizer, Garnier Nutrioniste Skin Renew, Lancome Blanc Expert High Resolution Resurface-C, Shiseido Brightening Emulsion, Olay Definity may also be used with the device of the present invention.

Another example for a use of the invention is wrinkle removal. The device 20 of the present invention may be used effectively and more conveniently for the removal or reduction and prevention of wrinkles. A wrinkle is a fold, ridge or crease in the skin. Skin wrinkles typically appear as a result of aging processes, loss of body mass, or temporarily, as the result of prolonged immersion in water. Age wrinkling in the skin is promoted by habitual facial expressions, aging, sun damage, smoking, poor hydration, and various other factors. Wrinkle removing treatments that can be used with the present invention include tretinoin, which is also known as Retin-A, which decreases cohesiveness of follicular epithelial cells. Additionally, tretinoin stimulates mitotic activity and increased turnover of follicular epithelial cells. Epidermal growth factor (EPG) may also be used. EPG is a small polypeptide of 53 amino acids and is a cytokine or cell messenger protein that stimulates epithelial cell proliferation. Taken internally, EPG is used to treat conditions in premature infants, as well as enlarged prostate. In cream form, EPG stimulates cell renewal but decreases collagen production in the skin. It is also helpful for wound and burn healing and has achieved amazing cures of severe ulcerating skin diseases. Another group of materials that can be used with the present invention are dermal fillers to correct wrinkles, and other depressions in the skin. Glycosaminoglycans (GAGs) may also be used with the present invention. GAGs are produced by the body to maintain structural integrity in tissues and to maintain fluid balance. Hyaluronic acid, which is a type of GAG that promotes collagen synthesis can be also employed. GAGs serve as a natural moisturizer and lubricant between epidermal layers. Topical glycosaminoglycans supplements can help to provide temporary restoration of enzyme balance to slow or prevent matrix breakdown and consequent onset of wrinkle formation. Botulinum toxin is a neurotoxin protein produced by the bacterium clostridium botulinum, which is frequently used to treat wrinkles as it immobilizes the muscles that caused the wrinkle. It can also be used with the present invention to treat wrinkles by delivering the toxin to the right depth and dispersing it conveniently along the route of the wrinkle. Commercially available materials that may be used as a material in the present invention for the treatment of wrinkles include Neutrogena Ageless Intensives® Anti-Wrinkle Deep Wrinkle Serum, Olay Regenerist Micro-Sculpting Cream, Clarins Contouring Facial Lift, and L'Oreal RevitaLift Deep-Set Wrinkle Repair.

It will be understood that many modifications can be made to the various disclosed embodiments without departing from the spirit and scope of the concept. For example, various sizes of the surgical devices are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments. Those skilled in the art will envision other modifications within the scope and spirit of the present invention.

I claim:

1. A microneedle system, comprising:
    a handle;
    a housing connected to the handle and having one or more cavities; each cavity adapted to receive one or more fluid/gel/cream material to be dispensed;
    a skin penetrating device in fluid connection with the one or more cavity; the skin penetrating device comprises:
        a base; and
        a number of protections extending from the base, wherein the protections are arranged in an array and wherein each projection comprises a tip for penetrating a surface of a biological surface; the skin penetrating device being configured to move relative to the housing;
    wherein movement of the skin penetrating device relative to the housing meters material from the one or more cavity onto the skin penetrating device;
    wherein the skin penetrating device is a cylindrical roller;
    wherein the housing includes a pusher element connected to a chamber element and configured such that the pusher element moves relative to the chamber element to push material from the one or more cavity through a slot in the chamber element; and
    wherein the cylindrical roller is connected to the chamber element with a first gear and the chamber element is connected to the pusher element with a second gear.

2. The microneedle system of claim 1 wherein the system includes more than one cavity for receiving one or more material to be dispensed.

3. The microneedle system of claim 1 wherein the one or more cavities are configured to receive material directly or in a removable container, cartridge, pouch or capsule.

4. The microneedle system of claim 1 further including at least one strip configured to dispense material.

5. The microneedle system of claim 4 wherein the strip is configured to dispense material in front of the skin penetrating device or in back of the skin penetrating device.

6. The microneedle system of claim 4 wherein the at least one strip is configured to dispense material different from the material disposed in the one or more cavities.

7. The microneedle system of claim 1 wherein the skin penetrating device is removable and interchangeable.

8. The microneedle system of claim 1 wherein the housing is removable and interchangeable.

9. The microneedle system of claim 1 wherein the cylindrical roller includes a spiral channel for evenly distributing material across the skin.

\* \* \* \* \*